(12) United States Patent
Clark et al.

(10) Patent No.: US 6,907,876 B1
(45) Date of Patent: Jun. 21, 2005

(54) DISPENSING APPARATUS COMPRISING A DOSAGE COUNTING DEVICE

(75) Inventors: John David Clark, King's Lynn (GB); Paul Michael Allsop, King's Lynn (GB); Christopher John Eames, King's Lynn (GB)

(73) Assignee: Bespak PLC, Norfolk (GB)

( * ) Notice: Subject to any disclaimer, the term of this patent is extended or adjusted under 35 U.S.C. 154(b) by 0 days.

(21) Appl. No.: 09/958,202

(22) PCT Filed: Mar. 28, 2000

(86) PCT No.: PCT/GB00/01180

§ 371 (c)(1),
(2), (4) Date: Nov. 13, 2001

(87) PCT Pub. No.: WO00/59806

PCT Pub. Date: Oct. 12, 2000

(30) Foreign Application Priority Data

Apr. 7, 1999 (GB) .............................................. 9907928

(51) Int. Cl.[7] .............................................. A61M 11/00
(52) U.S. Cl. .................................. 128/200.23; 222/38
(58) Field of Search ....................... 128/200.23, 203.12, 128/203.23; 604/58; 222/36, 38, 25, 28, 41, 402.1–402.25; 239/71, 74; 116/308, 309

(56) References Cited

U.S. PATENT DOCUMENTS

| 5,319,162 | A | * | 6/1994 | Ness ........................... 177/231 |
| 5,349,945 | A | | 9/1994 | Wass et al. ............ 128/200.23 |
| 6,516,799 | B1 | * | 2/2003 | Greenwood et al. ... 128/203.12 |
| 6,615,827 | B2 | * | 9/2003 | Greenwood et al. ... 128/200.23 |

FOREIGN PATENT DOCUMENTS

| CA | 2075128 | | 8/1996 | |
| GB | 2195544 A | * | 4/1988 | .......... A61M/11/00 |
| WO | wo98/56444 | | 12/1998 | |

\* cited by examiner

Primary Examiner—Weslun Lo
Assistant Examiner—Mital Patel
(74) Attorney, Agent, or Firm—Smith, Gambrell & Russell, LLP

(57) ABSTRACT

The present invention relates to dispensing apparatus comprising a housing (10) for receiving a pressurised container (15) containing product for dispensation, series of markings (172) indicative of quantities of product in the container, indicator means (160; 200) for indicating one of the markings of the series, and means for effecting relative movement between the indicator means and the series of markings on actuation of the pressurised container, so as to designate a subsequent marking of the series.

12 Claims, 5 Drawing Sheets

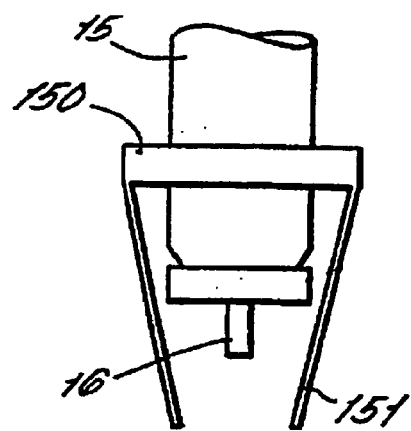
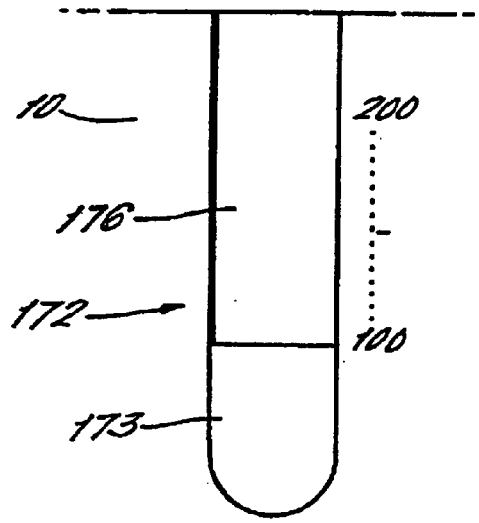
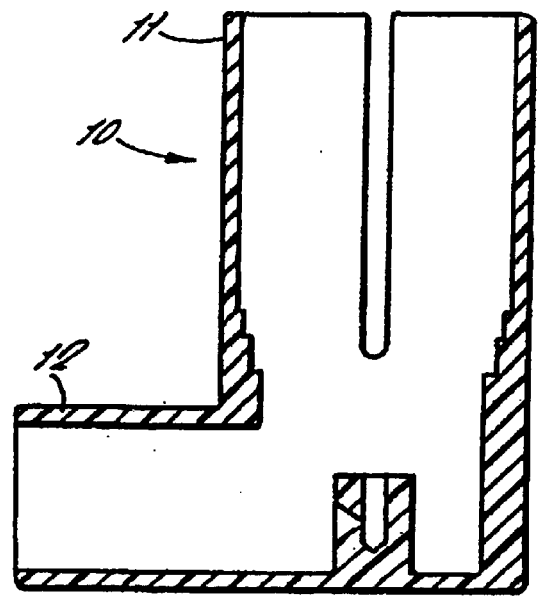

DISPENSING APPARATUS COMPRISING A DOSAGE COUNTING DEVICE

The present invention relates to improvements in dispensing apparatus and, in particular, to improvements in apparatus providing means for measuring the quantity of product remaining in a pressurised dispensing container.

Pressurised dispensing containers are widely used in the pharmaceutical industry for storing medications and other products to be dispensed in aerosol form. Such containers usually contain a propellant, such as HFC 134a, in which the product is suspended or dissolved. Solvents, such as ethanol, may also be present in the formulation. It is known to provide pressurised dispensing apparatus capable of dispensing metered doses of product from the containers upon each actuation of the container valve, for example, metered dose inhalers. The reliability and consistency of the metered dose is especially important where the product comprises or includes a medication. Inconsistent or unreliable dispensation could result in a user of the dispensing apparatus receiving too great or too little medication.

A problem found by many users of such apparatus is the inability to determine the quantity of product remaining in the container. Many types of apparatus continue to allow the dispensing of quantities of propellant and/or solvent when the container is nearly empty, even though the dose of product contained in the propellant is below the required level, thereby exacerbating the problem. Thus, users are often unaware that the dispensing apparatus is operating inadequately. This has potentially dangerous consequences where the product or medication dispensed is required urgently and no time is available to locate a replacement dispenser, such as in the treatment of asthmatic conditions. Sufferers of asthma often carry dispensers with them for extended periods of time, which may only be used on an occasional basis. Therefore, there is a danger that, where the user is unable to determine the contents of the pressurised dispensing container and the device is required in an emergency situation, the contents of the container may be inadequate.

U.S. Pat. No. 5,349,945 discloses a dispensing apparatus for receiving a pressurised container containing product for dispensation, a series of markings indicative of quantities of product in the container and indicator means for indicating one of the markings of the series wherein the indicator means is moved on actuation of the pressurised container to designate a subsequent marking of the series. WO-A-9856444 discloses another such dispensing apparatus.

It is an object of the present invention to provide apparatus for quickly and easily determining the quantity of product remaining in a pressurised dispensing container without the need for special testing equipment. Also, to provide apparatus suitable for use with conventional pressurised dispensing containers.

Accordingly, the present invention provides a dispensing apparatus comprising a housing (10) for receiving a pressurised container (15) containing product for dispensation, a series of markings (172) indicative of quantities of product in the contain r and indicator means (160; 200) for indicating on of the markings f the series, charact ris d in that a cylindrical member (140) is located in the housing (10), one of the housing and the cylindrical member being provided with a longitudinal slot (170) and the other of the housing and the cylindrical member having a helical channel (141) along its longitudinal axis, the indicator means (160; 200) being operatively connected to both the longitudinal slot and helical channel such that rotation of the cylindrical member relative to the housing on actuation of the pressurised container moves the indicator means along the longitudinal axis of the cylindrical member so as to designate a subsequent marking of the series.

The present invention also provides a dispensing apparatus comprising a housing (10) for receiving a pressurised container (15) containing product for dispensation, a series of markings (172) indicative of quantities of product in the container and indicator means (160, 200) for indicating one of the markings of the series, characterised in that one of the housing and the pressurised container (15) is provided with a longitudinal slot (170) and the other of the housing and the pressurised container is provided with a helical channel (141) along its longitudinal axis, the indicator means (160, 200) being operatively connected to both the longitudinal slot and helical channel such that rotation of the pressurised container relative to the housing on actuation of the pressurised container moves the indicator means along the longitudinal axis of the housing.

The present invention also provides a dispensing apparatus comprising a housing (10) for receiving a pressurised container (15) containing product for dispensation, a series of markings (172) indicative of quantities of product in the container and indicator means (160, 200) for indicating one of the markings of the series, characterised in that the housing is provided with a helical channel (141) along its longitudinal axis and a collar (155), the indicator means (160, 200) being operatively connected to the helical channel (141) and the collar (155) such that rotation of the collar (155) relative to the housing on actuation of the pressurised container moves the indicator means along the longitudinal axis of the housing.

The present invention also provides a dispensing apparatus comprising a housing (10) for receiving a pressurised container (15) containing product for dispensation, a series of markings (172) indicative of quantities of product in the container and indicator means (160, 200) for indicating one of the markings of the series characterised in that the housing (10) comprises a longitudinal slot (170) and the series of markings (172) are provided in a helical arrangement around the pressurised container (15) or other member (140; 155) located in the housing, such that only one of the series of markings is visible through the slot at any one time.

Embodiments of the present invention will now be described, by way of example only, with reference to the following drawings, in which:

FIG. 10 is a side elevation of the cap shown in FIG. 8 assembled with a dispensing device;

FIG. 11 is a schematic view of a part of the outer housing of the apparatus of FIG. 1;

FIG. 12 is a schematic cross-sectional view of the outer housing of the apparatus of FIG. 1;

Figure 1:
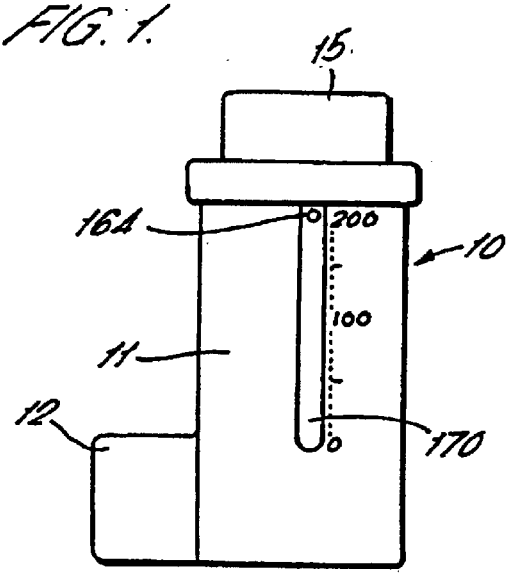
FIG. 1 is a side elevation of a first embodiment of dispensing apparatus according to the present invention.

FIGS. 1 to 12 show a dispensing apparatus according to the present invention. The apparatus comprises a housing 10 having a generally cylindrical portion 11, defining a chamber to slidably receive a pressurised dispensing container 15 and a mouthpiece 12, which extends laterally from a lower end of the cylindrical portion 11. The mouthpiece 11 may extend at a slight downward angle from the cylindrical portion 11. The pressurised dispensing container 15 comprises a metering valve attached to a can, for storing the product to be dispensed, by means of a ferrule which is placed over a valve stem of the metering valve and crimped to the open mouth of the can. A valve stem 16 extends axially from the metering valve and defines an outlet through which product is dispensed. The valve stem 16 is received in a valve stem receiving block 13 provided at a distal end of the generally cylindrical portion 11 as the dispensing container 15 is inserted therein. The valve stem receiving block 13 comprises a duct and an orifice such that product dispensed through the outlet of the valve stem 16 is directed through the duct and out of the orifice in the direction of the mouthpiece 12 in the form of an aerosol. Optionally the mouthpiece 12 may be covered by a mouthpiece cover when the apparatus is not being used, in order to protect the mouthpiece 12 from dust, dirt or other matter. In addition, the mouthpiece 12 may be detachable from the generally cylindrical portion 11 to allow for washing and cleaning of the mouthpiece. Preferably, the detachable portion would include the valve stem receiving block 13 which is the component most prone to becoming clogged with deposits from the pressurised dispensing container 15. An internal lip in the generally cylindrical portion 11 may be provided to retain the pressurised dispensing container 15 within the generally cylindrical portion 11 when the mouthpiece 12 is detached.

In the apparatus of the present invention the housing 10 is provided with means to indicate to a user of the apparatus the quantity of product in the pressurised dispensing container.

Figure 4:
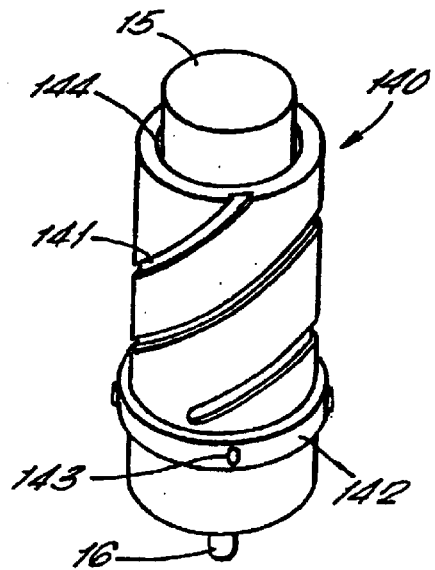
FIG. 4 is a perspective view of an inner housing of the apparatus of FIG. 1 containing a dispensing device.
Figure 5:
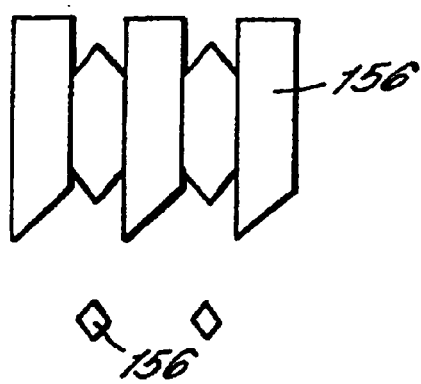
FIG. 5 is a schematic diagram of lugs of the apparatus of FIG. 1.

The apparatus comprises an inner cylindrical housing 140 open at both ends as shown in FIG. 4. The inner cylindrical housing 140 is provided with a number of inwardly directed ribs which act to reduce the effective diameter of the aperture. The other end 144 is unobstructed, as shown in FIG. 4. In use the pressurised dispensing container 15 is located in the inner housing 140 with valve stem 16 protruding through the aperture. The ribs prevent the container 15 from passing through the aperture. The pressurised dispensing container 15 may be inserted and removed from the inner housing 140, during assembly of the apparatus, through the aperture 144.

The inner housing 140 is provided with an annular flange 142. The flange 142 has a number of protrusions 143 equidistantly spaced around its circumference. An exterior surface of the inner housing 140 has a helical groove 141 extending from the large open end 144 to the flange 142.

Figure 2:
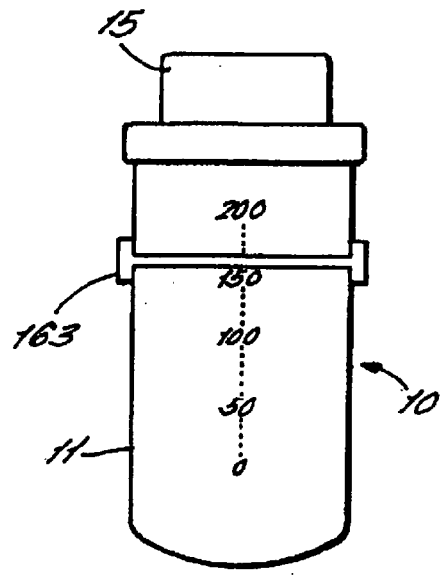
FIG. 2 is a rear elevation of a second embodiment of dispensing apparatus according to the present invention.
Figure 7:
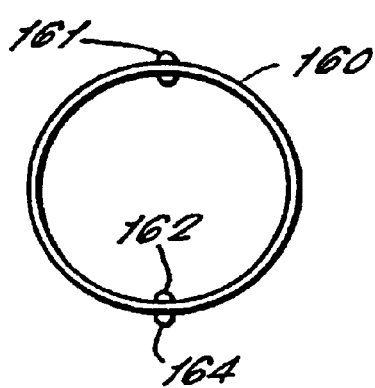
FIG. 7 is a plan view of a ring of the apparatus of FIG. 1.
Figure 9:
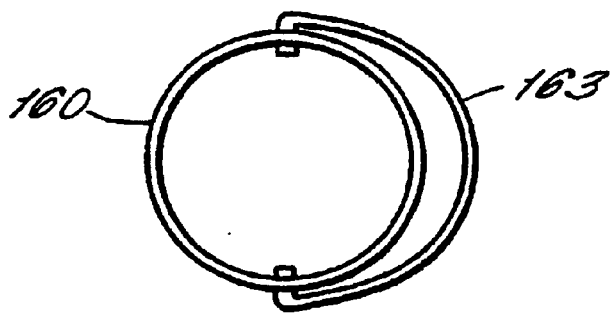
FIG. 9 is a plan view of another version of ring.

Around the inner housing 140 is located a ring 160. As shown in FIG. 7, the ring 160 has two pins 161 located on opposite sides thereof. The pins 161 penetrate the ring 160 or are two part elements having an outer portion 164 on an outer surface of the ring 160 and an inner portion 162 on an inner surface of the ring 160. The ring 160 is located around the inner housing 140 such that the inner portion 162 of each pin 161 is received in the groove 141 of the inner housing 140. The ring 160 is thus rotatable about and slidable along the inner housing 140 with the pins 161 constrained to move along helical groove 141. The ring 160 may, in addition, have an arcuate member 163 joined at each end to the outer portions 164 of each pin 161 as shown in FIGS. 2 and 9.

The cylindrical portion 11 of the housing 10 is provided with one or two longitudinally orientated slots 170, as shown in FIG. 1. The slots 170 may extend upwardly to contact the open end of the cylindrical portion 11 of housing 10 as shown in FIG. 12. The slots 170 may be provided with inserts 173 at their lower ends as shown in FIG. 11 to limit the degree to which the pins 161 may move down the slots 170. In this way the number of potential doses dispensed by the apparatus may be reduced so as to ensure that the apparatus is disposed of before there is any danger of reduction in the quantity of product dispensed in each dose. Alternatively the actuator may be moulded with a slot 170 or shorter length so as to reduce the number of potentially deliverable doses.

Figure 6:
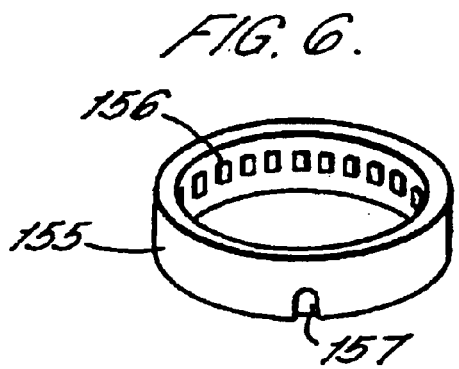
FIG. 6 is a perspective view of a collar of the apparatus of FIG. 1.

The housing 10 further comprises a collar 155, shown in FIG. 6, having a plurality of inwardly directed lugs 156. The lugs 156 have angled upper and lower surfaces, shown schematically in FIG. 5. An outer surface of the collar 155 comprises a notch 157. The internal diameter of the collar 155 is marginally greater than the external diameter of the flange 142 of the inner housing 140. The collar 155 is inserted in housing 10 near a lower end of cylindrical housing portion 11. Notch 157 engages a detent (not shown) on the cylindrical housing portion 11 to prevent rotational movement of the collar 155. Alternatively, collar 155 may be integrally moulded with the generally cylindrical portion 11. As an alternative the protrusions 143 may be provided as inwardly directed protrusions on the collar 155 and the lugs 156 may be provided as outwardly directed lugs on the flange 142.

Figure 3:
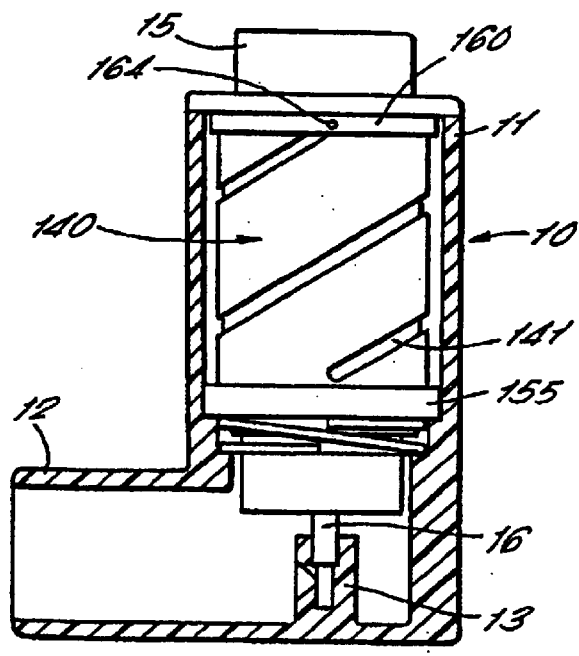
FIG. 3 is a sectional side elevation of the apparatus of FIG. 1.

The inner housing 140 is assembled with the main housing 10 such that the valve stem 16 of the pressurised dispensing container 15, which protrudes through the aperture of the inner housing 140 provided with the ribs, is received in the valve stem block 13, as shown in FIG. 3. A spring is provided between the inner housing 140 and the main housing 10 to bias the inner housing 140 upwardly away from the valve stem block 13. This may be achieved by means of a compression spring extending between the flange 142, or other part of inner housing 140, and a lower part of the housing 10 or by a tensile spring extending between the flange 142 and an upper part of the housing 10. Alternatively, the internal spring force of the metering valve of the pressurised dispensing container 15, which is used to bias the pressurised dispensing container 15, could be used to bias the inner housing 140 away from the valve stem receiving block 13.

The flange 142 is received in collar 155 with the flange protrusions 143 adjacent to, or contacting the inwardly directed collar lugs 156. The outer portions 164 of pins 161 of ring 160 are located in the slots 170 in the main housing 10 as shown in FIG. 1. In the embodiment provided with the arcuate member 163 attached to the ring 160, the arcuate member 163 is positioned around an exterior of the main housing 10 as shown in FIG. 2.

Figure 8:
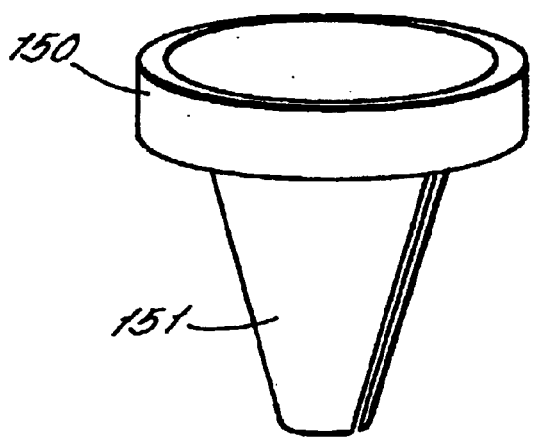
FIG. 8 is a perspective view of a cap of the apparatus of FIG. 1.

A cap 150 as shown in FIGS. 8 and 10 may be fitted over the open end of the housing 10 on the cylindrical portion 11 to retain the container 15, inner housing 140 and other components in position. The cap 150 comprises two flexible legs 151 which extend downwardly from cap 150 within the housing 10. The legs 151 flex apart as a pressurised dispensing container 15 is inserted through cap 150 into the inner housing 140. As the distal end of the legs pass over the ferrule of the pressurised dispensing container 15 they flex inwardly, thereby trapping the container 15 and preventing its withdrawal.

A push-button cap (not shown) may be provided as part of the main housing 10 to cover the upper portion of the pressurised dispensing container 15. Advantageously, this prevents the ingress of dust, contaminants and moisture into the apparatus.

Markings 172 are printed or embossed on an exterior surface of the housing 10 adjacent the slots 170. The markings 172 may comprise numbers indicating the quantity of product in the pressurised dispensing container 15 in terms of the number of dosages remaining. Alternatively they may comprise a series of descriptive statements indicating how full the pressurised dispensing container 15 is, such as "FULL", "¾ FULL", "½ FULL" etc.

Depression of the pressurised dispensing container 15 results in downward movement of the container 15 relative to the housing 10. As the container 15 moves downwardly, the inner housing 140 is caused to move downwardly such that the protrusions 143 contact the angled surfaces of the inwardly directed lugs 156 of collar 155. As a result the inner housing 140 is urged to incrementally rotate about its longitudinal axis. Since pins 161 are received in the slots 170 the ring 160 is incrementally moved vertically relative to the inner housing 140. As a result, the outer portions 164 of pins 160 and/or the arcuate member 163 are moved into alignment with a subsequent marking 172 indicating that the pressurised dispensing container 15 contains one less dose. The angled surfaces of the inwardly directed lugs 156 are dimensioned such that the inner housing 140 is urged to rotate on upward vertical movement of the protrusions 143, as occurs when the pressurised dispensing container 15 is released due to the biassing force of the spring, as well as downward vertical movement, as occurs when the pressurised dispensing container 15 is depressed.

When the pins 162 reach the bottom of the helical groove 141 the device locks-out preventing any further dispensation.

The following variations to the invention may advantageously be incorporated, either singly or in combination, in the apparatus described above.

The inner housing 140 may be dispensed with and the helical groove 141 be provided in the container wall of the pressurised dispensing container 15 and the protrusions 143 provided on the ferrule of the pressurised dispensing container 15.

The ring 160 may be replaced with a series of numbers of other markings spaced around the inner housing 140 or pressurised dispensing container 15 in a helical arrangement and spaced such that only a single number or marking is visible at any one time through the slots 170.

The inner housing may be non-rotatable and the collar 155 may be rotatable on interaction with the protrusions 143 of the inner housing 140. A series of markings or numbers are printed around the collar 155 and arranged such that at any one time a single number or marking is visible to a user of the apparatus through, for example, a sight window in the main housing 10.

Figure 13:
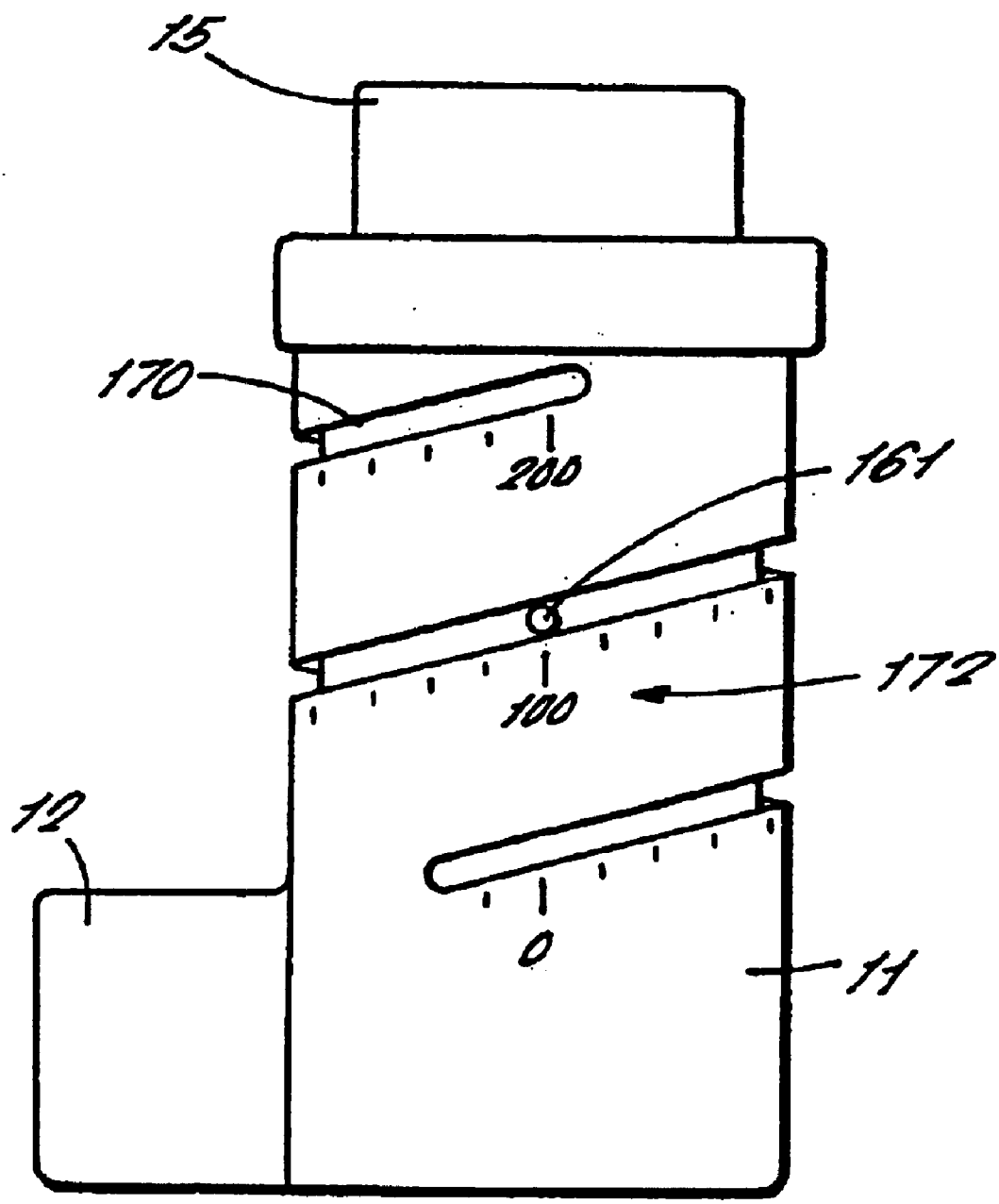
FIG. 13 is a side elevation of an alternative apparatus according to the present invention.

The inner housing 140 may be non-rotatable and a helical slot be provided in the generally cylindrical portion 11 of the main housing 10 in which the ring 160 is deployed as shown in FIG. 13. The ring 160 is operatively connected to the collar 155. Actuation of the apparatus causes the collar 155 and ring 160 to rotate about the inner housing 140 such that the pins 161 of the ring 160 move downwardly and around the helical slot.

Figure 14:
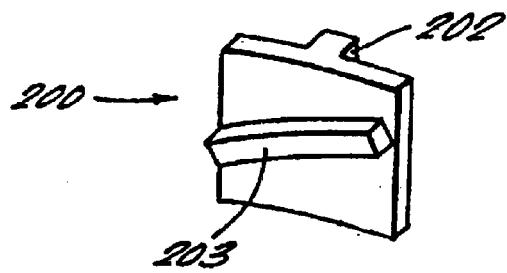
FIG. 14 is a perspective view of a marker of an alternative apparatus according to the present invention.
Figure 15:
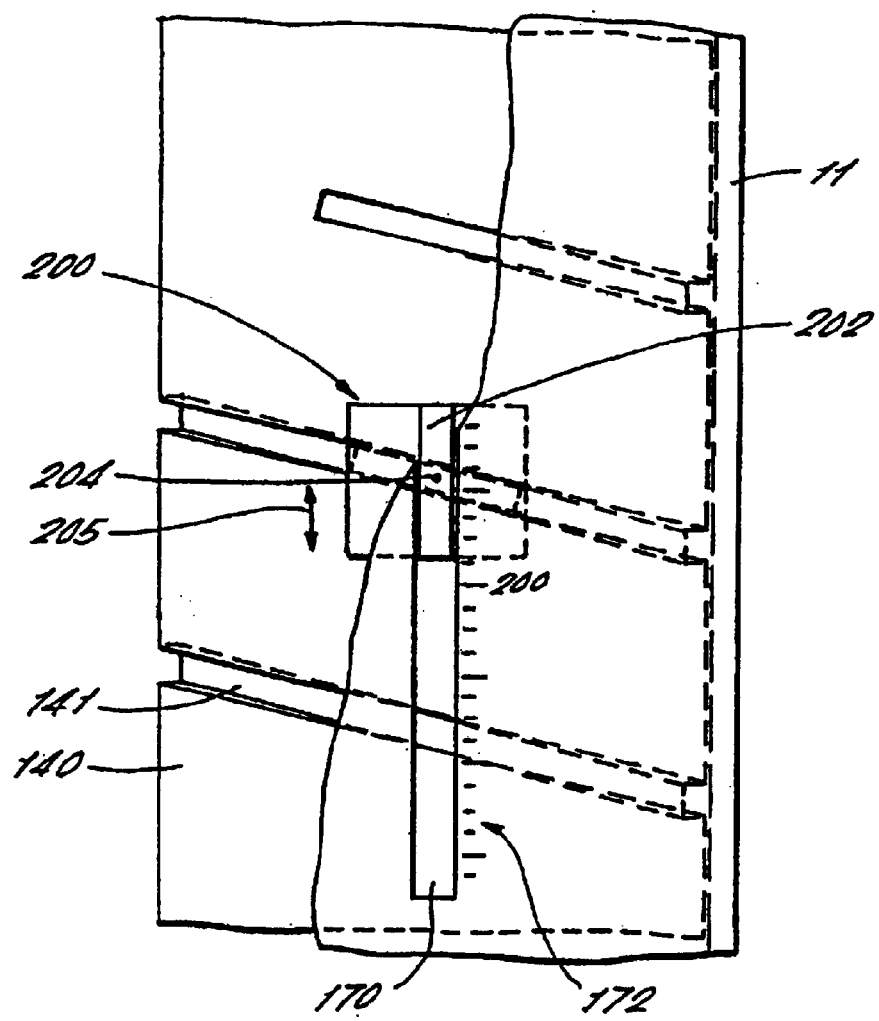
FIG. 15 is a side elevation, showing some hidden detail, of the marker of FIG. 14 assembled with the dispensing apparatus of the present invention.

The ring 160 may be replaced by a marker 200 having protrusions 202, 203 on each side as shown in FIG. 14. The inwardly directed protrusion 203 is disposed at an angle to the edges of the marker 200 such that it is received slidingly in the helical groove 141 of the inner housing. The outwardly directed protrusion 202 is disposed parallel to the edges of the marker 200 such that it is received slidingly in the vertical slot 170 of the main housing 10 when positioned between the inner housing 140 and the main housing 10 as shown in FIG. 15. An indicating dot 204 may be provided to indicate which marking 172 is designated.

Similarly to ring 160 relative movement of the inner housing 140 and the cylindrical portion 11 of the main housing 10 causes the marker 200 to move along the longitudinal axis of the cylindrical portion 11 in the direction of arrow 205.

The protrusions 143 and the collar 155 may be provided aligned with the top end of the inner housing 140 remote from the valve stem receiving block 13 rather than at the bottom end.

We claim:

1. Dispensing apparatus comprising a housing (10) for receiving a pressurised container (15) containing product for dispensation, a series of markings (172) indicative of quantities of product in the container and indicator means (160; 200) for indicating one of the markings of the series, characterised in that a cylindrical member (140) is located in the housing (10), one of the housing and the cylindrical member being provided with a longitudinal slot (170) and the other of the housing and the cylindrical member having a helical channel (141) along its longitudinal axis, the indicator means (160; 200) being operatively connected to both the longitudinal slot and helical channel such that rotation of the cylindrical member relative to the housing on actuation of the pressurised container moves the indicator means along the longitudinal axis of the cylindrical member so as to designate a subsequent marking of the series.

2. Dispensing apparatus as claimed in claim 1 wherein the housing (10) and the cylindrical member (140) are provided with co-operating formations (143, 156) having angled abutment surfaces such that relative longitudinal movement between the housing and the cylindrical member causes relative rotation between the housing and cylindrical member.

3. Dispensing apparatus comprising a housing (10) for receiving a pressurised container (15) containing product for dispensation, a series of markings (172) indicative of quantities of product in the container and indicator means (160, 200) for indicating one of the markings of the series, characterised in that one of the housing and the pressurised container (15) is provid d with a longitudinal sl t (170) and the other of the housing and the pressurised container is provided with a helical channel (141) along its longitudinal axis, the indicator means (160; 200) being operatively connected to both the longitudinal slot and helical channel such that rotation of the pressurised container relative to the housing on actuation of the pressurised container moves the indicator means along the longitudinal axis of the housing.

4. Dispensing apparatus as claimed in claim 3 wherein the housing (10) and the pressurised container (15) are provided with co-operating formations (143, 156) having angled abutment surfaces such that relative longitudinal movement between the housing and the pressurised container causes relative rotation between the housing and pressurised container.

5. Dispensing apparatus as claimed in claim 1 wherein the housing (10) comprises a collar (155) having one of the co-operating formations (143; 156) formed thereon.

6. Dispensing apparatus comprising a housing (10) for receiving a pressurised container (15) containing product for dispensation, a series of markings (172) indicative of quantities of product in the container and indicator means (160, 200) for indicating one of the markings of the series, characterised in that the housing is provided with a helical channel (141) along its longitudinal axis and a collar (155), the indicator means (160, 200) being operatively connected to the helical channel (141) and the collar (155) such that rotation of the collar (155) relative to the housing on actuation f the pressurised container moves the indicator means along the longitudinal axis of the housing.

7. Dispensing apparatus as claimed in claim 1 wherein the indicator means is a ring having one or mor pins located in the longitudinal slot (170) and the helical channel (141).

8. Dispensing apparatus as claimed in claim 1 wherein the indicator means is a marker (200) having a first protrusion (203) engaged in the helical channel (141) and a second protrusion (202) located in the longitudinal slot (170).

9. Dispensing apparatus comprising a housing (10) for receiving a pressurised container (15) containing product for dispensation, a series of markings (172) indicative of quantities of product in the container and indicator means (160, 200) for indicating one of the markings of the series characterised in that the housing (10) comprises a longitudinal slot (170) and the series of markings (172) are provided in a helical arrangement around the pressurised container (15) or other member (140; 155) located in the housing, such that only one of the series of markings is visible through the slot at any one time.

10. Dispensing apparatus as claimed in claim 1 comprising means (173) for locking out operation of the pressurised container after a pre-determined number of actuations.

11. Dispensing apparatus as claimed in claim 1 wherein the housing (10) comprises a mouthpiece (12) which is detachable.

12. Dispensing apparatus as claimed in claim 1 further comprising a pressurised dispensing container (15) located in the housing (10).

* * * * *